United States Patent [19]

Spears et al.

[11] Patent Number: 5,352,580

[45] Date of Patent: Oct. 4, 1994

[54] **SELECTIVE DETECTION OF MYCOBACTERIA BY NUCLEIC ACID PROBES DERIVED FROM *MYCOBACTERIUM KANSASII***

[75] Inventors: Patricia A. Spears, Raleigh; Daryl D. Shank, Durham, both of N.C.

[73] Assignee: Becton, Dickinson and Company, Franklin Lakes, N.J.

[21] Appl. No.: 889,651

[22] Filed: May 26, 1993

[51] Int. Cl.$^5$ .................. C12Q 1/68; C12P 19/34; C07H 21/04
[52] U.S. Cl. .................. 435/6; 435/91.2; 435/91.52; 536/24.32; 536/24.33; 935/78
[58] Field of Search ............... 435/6, 91, 91.2, 91.52; 536/27, 24.32, 24.33; 935/78

[56] References Cited

U.S. PATENT DOCUMENTS 5,168,039 12/1992 Crawford et al. ............... 435/6

OTHER PUBLICATIONS

Z. H. Huang, et al. "Identification of *Mycobacterium kansasii* by DNA Hybridization" *J. Clin. Microbiol.* 29:2125–2129 (1991).
J. W. Fries, et al. "Genus– and species–specific DNA probes to identify mycobacteria using the polymerase chain reaction" *Molec. Cell. Probes* 4:87–105 (1990).
A. J. Hance, et al. "Detection and identification of mycobacteria by amplification of mycobacterial DNA" *Molec. Microbiol.* 3:843–849 (1989).
Spears et al. Abstracts of the General Meeting—1992: Abstract No. 04, ASM, 1992.

*Primary Examiner*—Margaret Parr
*Assistant Examiner*—Lisa Arthur
*Attorney, Agent, or Firm*—Donna R. Fugit

[57] ABSTRACT

Oligonucleotide probes derived from *Mycobacteria Kansasii* capable of selectively hybridizing to Mycobacteria nucleic acid are disclosed. The oligonucleotide probe is selected from the group consisting of: (a) an oligonucleotide probe consisting essentially of the DNA sequence given herein as SEQ ID NO:1 (MK14); (b) oligonucleotide probes comprising fragments of MK14 which retain the capability of MK14 of selectively hybridizing to Mycobacteria nucleic acid; (c) oligonucleotide probes which hybridize to MK14 and are capable of selectively hybridizing to Mycobacteria nucleic acid; and (d) oligonucleotide probes which are complementary to any of the foregoing and are capable of selectively hybridizing to Mycobacteria nucleic acid. The probes are useful in nucleic acid amplification and hybridization assays for genus-specific detection of the mycobacteria, specific detection of *M. kansasii* and specific detection of the slow-growing mycobacteria. Methods of using the probes to detect and amplify Mycobacteria nucleic acid and kits containing the same are also disclosed.

31 Claims, 3 Drawing Sheets

FRAGMENT BC

SELECTIVE DETECTION OF MYCOBACTERIA BY NUCLEICACID PROBES DERIVED FROM *MYCOBACTERIUM KANSASII*

FIELD OF THE INVENTION

The present invention relates to oligonucleotide probes, and particularly relates to oligonucleotide probes capable of selectively hybridizing to Mycobacteria DNA.

BACKGROUND OF THE INVENTION

Health care providers are encountering a significant increase in cases of mycobacterial infections. Many of these new cases are related to the AIDS epidemic. Physicians rely on clinical microbiologists to assist then in diagnosing a mycobacterial infection. The diagnosis of such infections is, however, largely dependent on acid-fast staining and cultivation of the organism, followed by biochemical assays. These are time consuming processes. Hence, there is a continuing need for new, and particularly rapid, methods of diagnosing mycobacterial infections.

SUMMARY OF THE INVENTION

The present invention provides an oligonucleotide probe capable of selectively hybridizing to Mycobacteria nucleic acid. The oligonucleotide probe is selected from the group consisting of: (a) an oligonucleotide probe consisting essentially of the DNA sequence given herein as SEQ ID NO:1 (MK14): oligonucleotide probes comprising fragments of MK14 which retain the capability of MK14 of selectively hybridizing to Mycobacteria nucleic acid; (c) oligonucleotide probes which hybridize to MK14 and are capable of selectively hybridizing to Mycobacteria nucleic acid; and (d) oligonucleotide probes which are complementary to any of the foregoing and are capable of selectively hybridizing to Mycobacteria nucleic acid.

A first embodiment of the foregoing is an oligonucleotide probe selected from the group consisting of: (a) an oligonucleotide probe consisting essentially of the DNA sequence given herein as SEQ ID NO:22 (*M. Kansasii* fragment BC), an oligonucleotide probe consisting essentially of the DNA sequence given herein as SEQ ID NO:23 (*M. tuberculosis* fragment BC), and an oligonucleotide probe consisting essentially of the sequence given herein as SEQ ID NO:24 (*M. avium* fragment BC); (b) oligonucleotide probes comprising fragments of probes of (a) above which retain the capability of probes of (a) above of selectively hybridizing to Mycobacteria nucleic acid; (c) oligonucleotide probes which hybridize to probes of (a) above and are capable of selectively hybridizing to Mycobacteria nucleic acid; and (d) oligonucleotide probes which are complementary to any of the foregoing and are capable of selectively hybridizing to Mycobacteria nucleic acid.

A second embodiment of the foregoing is an oligonucleotide probe selected from the group consisting of: (a) an oligonucleotide probe consisting essentially of the DNA sequence given herein as SEQ ID NO:14 (MK14-C); (b) oligonucleotide probes comprising fragments of MK14-C which retain the capability of MK14-C of selectively hybridizing to Mycobacteria nucleic acid; (c) oligonucleotide probes which hybridize to MK14 and are capable of selectively hybridizing to Mycobacteria nucleic acid; and (d) oligonucleotide probes which are complementary to any of the foregoing and are capable of selectively hybridizing to Mycobacteria nucleic acid.

A third embodiment of the foregoing is an oligonucleotide probe capable of selectively hybridizing to *Mycobacteria kansasii* nucleic acid, the oligonucleotide probe selected from the group consisting of: (a) an oligonucleotide probe consisting essentially of the DNA sequence given herein as SEQ ID NO:15 (MK14-D); (b) oligonucleotide probes comprising fragments of MK14 which retain the capability of MK14-D of selectively hybridizing to *Mycobacteria kansasii* nucleic acid; (c) oligonucleotide probes which hybridize to MK14 and are capable of selectively hybridizing to *Mycobacteria kansasii* nucleic acid; and (d) oligonucleotide probes which are complementary to any of the foregoing oligonucleotide probes and are capable of selectively hybridizing to Mycobacteria nucleic acid.

A method of detecting Mycobacteria nucleic acid in a nucleic acid sample is also disclosed herein. The method comprises the steps of contacting an oligonucleotide probe to a nucleic acid sample under conditions permitting the hybridization of said oligonucleotide probe to Mycobacteria nucleic acid, wherein the oligonucleotide probe is a probe as given above, and then detecting whether or not the oligonucleotide probe hybridizes to the nucleic acid sample, the hybridization of the oligonucleotide probe to the nucleic acid sample indicating that the nucleic acid sample contains Mycobacteria nucleic acid.

Also disclosed herein is a kit for detecting Mycobacteria nucleic acid in a nucleic acid sample. The kit comprises a hybridization solution together with an oligonucleotide probe as given above. The oligonucleotide probe may be either lyophylized or carried in the hybridization solution.

A method of amplifying a selected Mycobacteria nucleic acid sequence in a nucleic acid sample is also disclosed herein. The amplification method comprises contacting at least one pair of oligonucleotide probes to the nucleic acid sample under conditions permitting the hybridization of each of the oligonucleotide probes to the selected Mycobacteria nucleic acid sequence, wherein said pair of probes together comprise an amplification pair, and wherein each of said oligonucleotide probes is selected from the group consisting of (i) oligonucleotide probes comprising fragments of SEQ ID NO:1 (MK14) which retain the capability of MK14 of selectively hybridizing to Mycobacteria nucleic acid; (ii) oligonucleotide probes which hybridize to MK14 and are capable of selectively hybridizing to Mycobacteria nucleic acid; and (iii) oligonucleotide probes which are complementary to any of the foregoing and are capable of selectively hybridizing to Mycobacteria nucleic acid; and then amplifying the selected Mycobacteria target sequence.

DETAILED DESCRIPTION OF THE INVENTION

Figure 1:
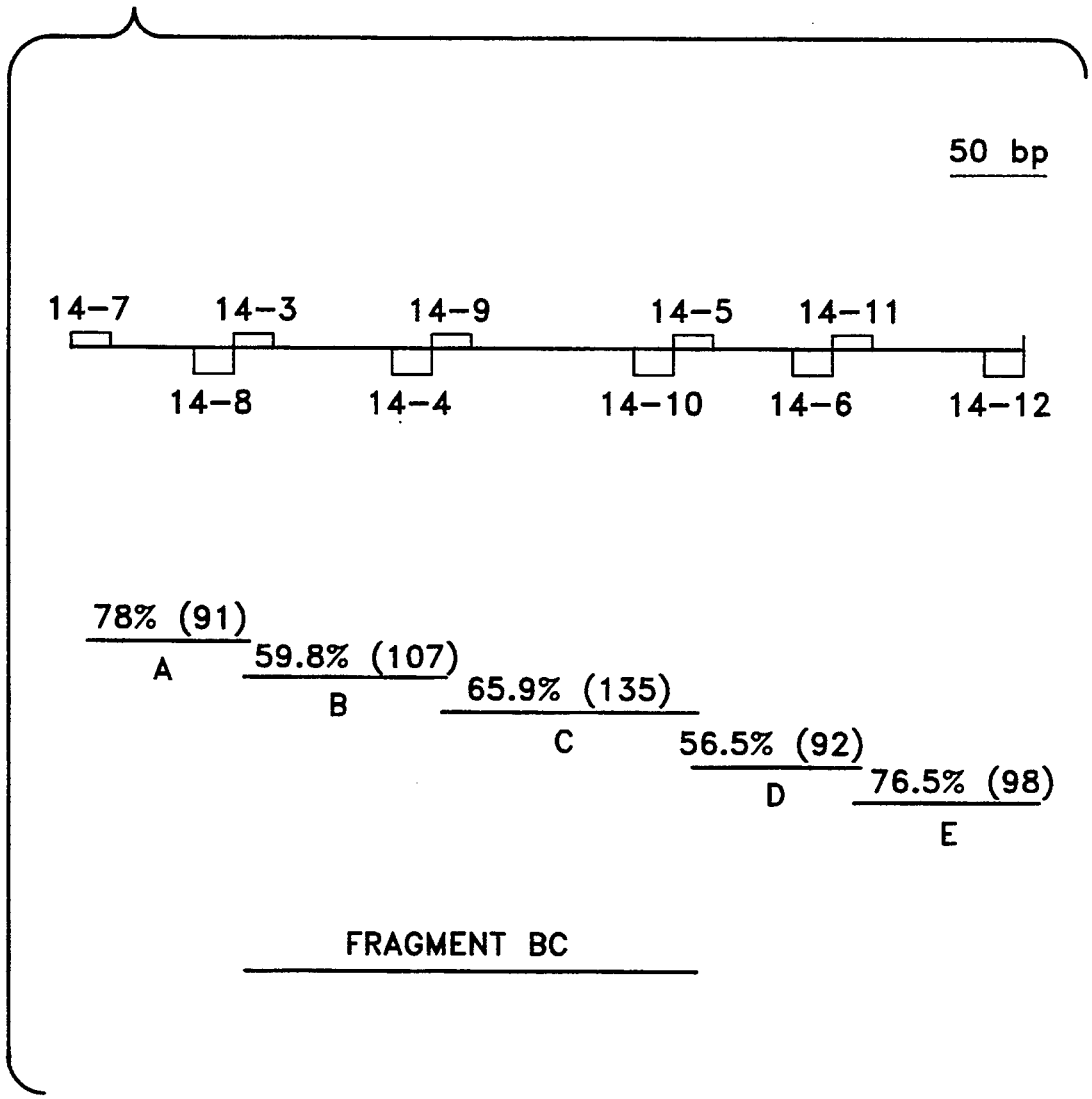
FIG. 1 shows a map of clone MK14. The insert of plasmid MK14 was subdivided into 5 subfragments A-E. Along the DNA are oligonucleotides (oligos) designated as boxes and labeled as per oligo list (table 1 below). Each fragment size and GC content is as noted.

The present invention advantageously provides both probes which bind to a variety of different Mycobacteria species and probes which bind to specific Mycobacteria species. The general probes are useful as an initial screen for Mycobacterial infection, and provide a rapid alternative to the culturing techniques currently employed as an initial screen, which require on the order of six weeks of culturing. Once a positive result on the initial screen is found, the species specific probes herein provide a rapid means to diagnose the particular infection.

Nucleotide sequences are presented herein by single strand only, in the 5' to 3' direction, from left to right. One letter nucleotide symbols used herein have their standard meaning in the art in accordance with the recommendations of the IUPAC-IUB Biochemical Nomenclature Commission.

The term "mycobacteria" as used herein has its conventional meaning in the art referring to acid-fast, non-motile, rod shaped bacteria. See generally B. Davis et al., Microbiology, 724–742 (3d Ed. 1980). By way example, the mycobacteria include, but are not limited to, *Mycobacterium africanum, M. avium, M. bovis, M. bovis-BCG, M. chelonae, M. fortuitum, M. gordonae, M. intracellulare, M. kansasii, M. microti, M. scrofulaceum,* and *M. tuberculosis.*

The term "amplification pair," as used herein, refers to a pair of oligonucleotide probes of the present invention selected to be suitable for use together in amplifying a selected mycobacteria nucleic acid sequence by a process such as polymerase chain reaction, ligase chain reaction, or strand displacement amplification, as explained in greater detail below.

Nucleic acid (i.e., DNA or RNA) samples for practicing the present invention may be obtained from any suitable source. Typically, the nucleic acid sample will be obtained in the form of a sample of a biological fluid or biological tissue suspected of containing mycobacteria. Suitable biological fluids include, but are not limited to, sputum, bronchial washings, gastric washings (containing swallowed sputum), blood, milk, and lymph fluid. Suitable tissue samples include, but are not limited to, skin and soft tissue samples. As mycobacteria infect both human and animal species, the present invention is applicable to both human and veterinary diagnostic procedures, and samples may be collected from both human and animal species. For example, *M. bovis* causes tuberculosis in cattle and is transmissible to humans, and hence the present invention may be used to diagnosis infection in cattle and to test cattle milk for the presence of *M. bovis* which may be transmitted to humans. Another example is *M. avium* and *M. intracellulare*, which infect birds (e.g., chickens and pigeons) as well as swine, and hence the present invention may be used to detect such infections. Further, humans are susceptible to infection from a variety of mycobacteria, including, but not limited to, *M. tuberculosis, M. kansasii, M. avium, M. intracellulaire, M. scrofulaceum* and *M. fortuitum*, and the present invention may be used to detect such infections.

Oligonucleotide probes of the present invention may be of any suitable length, depending on the particular assay format employed. In general, the oligonucleotide probes are at least 10 to 15 nucleotides in length. For example, oligonucleotide probes used for detecting Mycobacteria are preferably 15 to 20 nucleotides in length. The oligonucleotide probes may incorporate the elements of a strand displacement amplification probe, as explained in detail below. Nucleic acid sequences to which amplification pairs of oligonucleotide probes are directed are preferably 50 to 150 nucleotides in length.

With respect to nucleic acid sequences which hybridize to specific nucleic acid sequences disclosed herein, hybridization may be carried out under conditions of reduced stringency, medium stringency or even stringent conditions (e.g., conditions represented by a wash stringency of 0.5x SSC and 0.1% SDS at a temperature of 20 or 30 degrees below the melting temperature of the probe, or even conditions represented by a wash stringency of 0.1x SSC and 0.1% SDS at a temperature of 10 degrees below the melting temperature of the DNA sequence to MK14 DNA) in a standard hybridization assay. See J. Sambrook et al., Molecular Cloning, A Laboratory Manual (2d Ed. 1989)(Cold Spring Harbor Laboratory)). In general, nucleic acid sequences which hybridize to the MK14 DNA disclosed herein will have at least 65% sequence similarity, 70% sequence similarity and even 75% or greater sequence similarity with the sequence of MK14 DNA disclosed herein.

Probes of the invention can be utilized with naturally occurring sugar-phosphate backbones as well as modified backbones including phosphorothioates, dithionates, alkyl phosphonates and α-nucleotides. Modified sugar-phosphate backbones are generally illustrated by Miller and T'so, *Ann. Reports Med. Chem.*, 23:295 (1988) and Moran et al., *Nuc. Acids Res.*, 14:5019 (1987). Probes of the invention can be constructed of either ribonucleic acid (RNA) or deoxyribonucleic acid (DNA), with DNA preferred.

Use of probes in detection methods include Northern blots (RNA detection), Southern blots (DNA detection), western blots (protein detection), and dot blots (DNA, RNA or protein). Other detection methods include kits containing probes on a dipstick setup and the like.

To detect hybrid molecules formed from using the probes of the invention, typically a detectable marker is added to one of the probes. Probes can be labelled by several methods. Probes can be radiolabelled and detected by autoradiography. Such labels for autoradiography include $^3H$, $^{125}I$, $^{35}S$, $^{14}C$, and $^{32}P$. Typically the choice of radioactive isotopes depends on research preferences involving ease of synthesis, stability, and half lives of the isotopes. Other detectable markers include ligands, fluorophores, chemiluminescent agents, electrochemical via sensors, time-resolved fluorescence, enzymes, and antibodies. For example, an antibody can be labelled with a ligand. Other detectable markers for use with probes of the invention include biotin, radionucleotides, enzyme inhibitors, co-enzymes, luciferins, paramagnetic metals, spin labels, and monoclonal antibodies. The choice of label dictates the manner in which the label is bound to the probe.

Radioactive nucleotides can be incorporated into probes of the invention by several means. Such means include nick translation of double-stranded probes, copying single-stranded M13 plasmids having specific inserts with the Klenow fragment of DNA polymerase I of *E. coli* or other such DNA polymerase in the presence of radioactive dNTP, transcribing cDNA from RNA templates using reverse transcriptase in the presence of radioactive dNTP, transcribing RNA from vectors containing strong promoters such as SP6 promoters or T7 promoters using SP6 or T7 RNA polymerase in the presence of radioactive rNTP, tailing the 3' ends of probes with radioactive nucleotides using terminal transferase, and by phosphorylation of the 5' ends of probes using gamma $^{32}P$ ATP and polynucleotide kinase.

Amplification of a selected, or target, nucleic acid sequence may be carried out by any suitable means. See generally D. Kwoh and T. Kwoh, *Am. Biotechnol. Lab.* 8, 14–25 (1990). Examples of suitable amplification techniques include, but are not limited to, polymerase chain reaction, ligase chain reaction, strand displacement amplification, transcription-based amplification (see D. Kwoh et al., *Proc. Natl. Acad Sci.* USA 86, 1173–1177 (1989)), self-sustained sequence replication (see J. Guatelli et al., *Proc. Natl. Acad. Sci.* USA 87, 1874–1878 (1990)), and the Qβ replicase system (see P. Lizardi et al., *BioTechnology* 6, 1197–1202 (1988)).

Polymerase chain reaction (PCR) is carried out in accordance with known techniques. See, e.g., U.S. Pat. Nos. 4,683,195; 4,683,202; 4,800,159; and 4,965,188 (the disclosure of all U.S. Patent references cited herein are to be incorporated herein by reference). In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized which is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques.

Ligase chain reaction (LCR) is carried out in accordance with known techniques. See, e.g., R. Weiss, *Science* 254, 1292 (1991). In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

Strand displacement amplification (SDA) is also carried out in accordance with known techniques. See G. Walker et al., *Proc. Natl. Acad. Sci.* USA 89, 392–396 (1992); G. Walker et al., *Nucleic Acids Res.* 20, 1691–1696 (1992). SDA may be carried out with a single amplification primer or a pair of amplification primers, with exponential amplification being achieved with the latter. In general, SDA amplification primers comprise, in the 5' to 3' direction, a flanking sequence (the DNA sequence of which is noncritical), a restriction site for the restriction enzyme employed in the reaction, and an oligonucleotide sequence (e.g., an oligonucleotide probe of the present invention) which hybridizes to the target sequence to be amplified and/or detected. The flanking sequence, which simply serves to facilitate binding of the restriction enzyme to the recognition site, is preferably about 15 to 20 nucleotides in length; the restriction site is functional in the SDA reaction (i.e., phosphorothioate linkages incorporated into the primer strand do not inhibit subsequent nicking—a condition which may be satisfied through use of a nonpalindromic recognition site); the oligonucleotide probe portion is preferably about 13 to 15 nucleotides in length. SDA is carried out with a single amplification primer as follows: a restriction fragment (preferably about 50 to 100 nucleotides in length and preferably of low GC content) containing the sequence to be detected is prepared by digesting a DNA sample with one or more restriction enzymes, the SDA amplification primer is added to a reaction mixture containing the restriction fragment so that a duplex between the restriction fragment and the amplification primer is formed with a 5' overhang at each end, a restriction enzyme which binds to the restriction site on the amplification probe (e.g., HincII) is added to the reaction mixture, an exonuclease deficient DNA polymerase (e.g., an exonuclease deficient form of *E. coli* DNA polymerase I, see V. Derbyshire, *Science* 240, 199–201 (1988)) is added to the reaction mixture, and three dNTPs and one dNTP[αS], with the dNTP[αS] selected so that a phosphorothioate linkage is incorporated into the primer strand at the restriction site for the particular restriction enzyme employed (e.g., dGTP, dCTP, dTTP, and dATP[αS] when the restriction enzyme is HincII) are added to the reaction mixture. The DNA polymerase extends the 3' ends of the duplex with the dNTPs to form a downstream complement of the target strand, the restriction enzyme nicks the restriction site on the amplification primer, and the DNA polymerase extends the 3' end of the amplification primer at the nick to displace the previously formed downstream complement of the target strand. The process is inherently repetitive because the restriction enzyme continuously nicks new complementary strands as they are formed from the restriction site, and the DNA polymerase continuously forms new complementary strands from the nicked restriction site. SDA can be carried out with a pair of primers on a double stranded target DNA sequence, with the second primer binding to the 5' end of the complementary strand, so that two sets of repetitive reactions are occuring simultaneously, with the process proceeding exponentially because the products of one set of reactions serve as a target for the amplification primer in the other set of reactions. In addition, the step of first digesting the DNA sample to form a restriction fragment can be eliminated by exploiting the strand displacing activity of the DNA polymerase and adding a pair of "bumper" primers which bind to the substrate at a flanking position 5' to the position at which each amplification primer binds. Each bumper primer extension product displaces the corresponding amplification primer extension product, and the two displaced, complementary, amplification primer extension products bind to one another to form a double-stranded DNA fragment which can then serve as a substrate for exponential SDA with that pair of SDA primers.

When SDA is employed, the oligonucleotide probes of the invention are preferably selected so that guanine plus cytosine content is low, preferably comprising less than 70% of the total nucleotide composition of the probe. Similarly, the target sequence should be of low GC content to avoid the formation of secondary structures.

A kit for detecting mycobacteria nucleic acid in a nucleic acid sample contains at least one probe of the present invention, and hybridization solution for enabling hybridization between the probes and the nucleic acid sample, with the probe either suspended in the solution or provided separately in lyophylized form. One example of a suitable hybridization solution is a solution comprised of 6x SSC (0.9M sodium chloride, 0.09M sodium citrate, pH 7.0), 0.1M EDTA pH 8.0, 5x Denhardt's solution [0.1% (w/v) Ficoll Type 400, 0.1% (w/v) polyvinylpyrrolidone, 0.1% (w/v) bovine serum albumin], and 100 µg/ml sheared, denatured salmon sperm DNA, commercially available from Bethesda Research Laboratories, Gaithersburg, Md. 20877 USA under Catalog No. 5565UA. See also T. Maniatis et al., Molecular Cloning: A Laboratory Manual, 387–388 (1982)(Cold Spring Harbor Laboratory). The components of the kit are packaged together in a common container (e.g., a container sealed with a frangible seal), the kit typically including an instruction sheet for carrying out a specific embodiment of the method of the present invention. Additional optional components of the kit, depending on the assay format to be employed, include a second probe of the invention suitable for use with the first probe for carrying out PCR as explained above (or, in the case of a kit for carrying out LCR, two pairs of probes of the present invention), one or more detection probes, and means for carrying out a detecting step (e.g., a probe of the invention labelled with a detectable marker and optionally an enzyme substrate when the detectable marker is an enzyme).

The present invention is explained in greater detail in the following Examples, in which "Kb" means kilobases, "bp" means base pairs, "ng" means nanograms, "pmoles" means picomoles, "µl" means microliters, "mM" means milliMolar, "µM" means microMolar, "DTT" means dithiothreitol, "Tm" means melting temperature, and temperatures are given in degrees Centigrade unless otherwise indicated. These Examples are for illustrative purposes only, and are not to be taken as limiting of the invention.

EXAMPLE 1

Strains and Genomic DNA Preparation

Mycobacteria used in the Examples described herein were M. africanum LCDC501, M. avium ATCC25291, M. bovis CDC4, M. bovis-BCG CDC34, M. chelonae TMC1543, M. fortuitum TMC1529, M. gordonae TMC1318, M. intracellulare ATCC13950, M. kansasii TMC1201, M. microti LCDC201, M. scrofulaceum CDC78, and M. tuberculosis ATCC27294. Non-mycobacteria used were Bordetella pertussis ATCC8467, Candida albicans ATCC44808, Corynebacterium diphtheriae ATCC11913, Escherichia coli ATCC11775, Flavobacterium meningisepticum ATCC13253, Nocardia asteroides ATCC3308, Rhodococcus rhodochrous ATCC13808, Streptococcus pnuemoniae ATCC6303, Adenovirus Sigma D3390 (Advirus), Eukaryotic DNA McCoy cells (eukDNA). The slow growing mycobacteria are M. africanum, M. avium, M. Bovis, M. bovis-BCG, M. intracellulare, M. kansasii, M. microti, M. scrofulaceum, and M. tuberculosis. The fast growing mycobacteria are M. chelonae, M. fortuitum, and M. gordonae. All of the mycobacteria strains were cultured in BACTEC vials then heat killed at 70° C. for 4 hours. The genomic DNA was isolated in accordance with known techniques. See S. Visuvanathan et al., Simple Enzymatic Method for Isolation of DNA from Diverse Bacteria, J. Microbiol. Meth. 10, 59–64 (1989). The non-mycobacteria strains were cultured in Luria broth and the genomic DNA was isolated by the CTAB mini-prep method. See, e.g., F. Asubel et. al., Current Protocols in Molecular Biology (1987).

EXAMPLE 2

M. kansasii Library

M. kansasii genomic DNA was cut with Sau3AI (GIBCO BRL). The fragment sizes ranged from 1.4 Kb to <200 bp. The vector, BlueScript SK+ (Stratagene), was digested with BamHI (GIBCO BRL) and then phosphatased using Alkaline Phosphatase from calf intestine (CIAP) (Boehringer Mannheim Biochemicals). 750 ng of insert was ligated to 20 ng of vector in 50 mM Tris-HCl pH 7.5, 7 mM MgCl$_2$, 1 mM DTT, 1 mM ATP and 1 Unit/10 µT4 DNA Ligase (GIBCO BRL). The ligation was incubated at 15° C. overnight then transformed into competent JM109 cells (Stratagene). 1000 independent isolates were obtained.

EXAMPLE 3

Identification and Sequencing of Clone MK14

From the 1000 clones generated in Example 2 above, 15 were chosen for screening genomic blot which consisted of various mycobacterial and non-mycobacterial DNA's. Of the 15 clones, MK14 (SEQ ID NO:1) was found to hybridize to all the mycobacteria and not cross hybridize to any non-mycobacteria tested. Plasmid pMK14 containing SEQ ID NO:1 (MK14) has been deposited with the American Type Culture Collection, Rockville, Md. under the Accession Number 75455 on Apr. 27, 1990.

MK14 was sequenced using a Sequenase version 2.0 kit (United States Biochemicals) with [α-35S]-deoxyadenosine triphosphate (NEN-DuPont). MK14 was also sequenced using the Applied Biosystems 373A DNA Sequencer using the dye primer kit as suggested by the manufacturer.

EXAMPLE 4

Oligonucleotide Synthesis

Oligonucleotides (oligos) were synthesized on an Applied Biosystems 380B Synthesizer as suggested by the manufacturer. The oligos were deblocked at 50° C. and then purified through an Oligonucleotide Purification Cartridge as suggested by the manufacturer. Names and sequences of oligonucleotides are listed in Table 1.

TABLE I

Oligonucleotides

| | |
|---|---|
| 14-3 | ACC TGT GTG CCA CCA CAC CA (SEQ ID NO: 2) |
| 14-4 | ATA CGG TCA TCG GCT ACC TG (SEQ ID NO: 3) |
| 14-5 | AAC GAA CTC GTT GAC GGG AC (SEQ ID NO: 4) |
| 14-6 | ATT CCT GCG GGT TTT CTT CA (SEQ ID NO: 5) |
| 14-7 | GGC TCC GGC GAA CGA TTC CG (SEQ ID NO: 6) |
| 14-8 | CGA CGC GTC GGG TTC GCC GC (SEQ ID NO: 7) |
| 14-9 | GAG CCC CCG CAC GCC GTA GT (SEQ ID NO: 8) |
| 14-10 | CGC CGC TCC ACC TTG TGC TG (SEQ ID NO: 9) |
| 14-11 | GGG CGC GCA TGG CTC AGG GG (SEQ ID NO: 10) |
| 14-12 | GGC GCT GAC GAC CAC GTG GT (SEQ ID NO: 11) |

Note that, with respect to oligonucleotide 14-3 (SEQ ID NO:2), the T at the position corresponding to position 98 in MK14 (SEQ ID NO:1) is absent because the synthesis of this probe was based on earlier sequence information. While this change is incorporated into MK14 fragments synthesized with this oligonucleotide (discussed below), no adverse effect was seen.

EXAMPLE 5

Production of MK14 Fragments A to E by Polymerase Chain Reaction

Clone MK14 was divided into five smaller fragments designated A to E by polymerase chain reaction using plasmid MK14 as the template and the oligonucleotides primers described in Example 4 above in the pattern shown in FIG. 1.

Polymerase chain reaction amplifications were done in 25–100 μl reactions consisting of 10 mM Tris-HCl pH 8.3, 50 mM KCl, 1.5 mM MgCl2, 0.001% (w/v) gelatin, 200 μM dATP, 200 μM dCTP, 200 μM dGTP, 200 μM dTTP, 1.0 μM each primer, 100 ng/100 ul genomic DNA as template or 50 ng/100 μl plasmid DNA as template. The reactions were overlaid with mineral oil and heated to 95° C. for 5 minutes. 2.5 Units/100 μl AmpliTaq polymerase (Perkin Elmer Cetus) was added and the cycling was started. The samples were typically incubated 94° C. for 1 minute and 30 seconds, 37°–50° C. for 2 minutes, 72° C. for 3 minutes for 25–30 cycles. This was followed by a 7 minute at 72° C. incubation then stored at 4° C.

Fragment A (SEQ ID NO:12) consisted of nucleotides 5–95 of MK14; fragment B (SEQ ID NO:13) consisted of nucleotides 96–202 of MK14 (note comment: in Example 4 above); fragment C (SEQ ID NO:14) consisted of nucleotides 203–337 of MK14; fragment D (SEQ ID NO:15) consisted of nucleotides 338–429 of MK14; and fragment E (SEQ ID NO:16) consisted of nucleotides 430–527 of MK14.

EXAMPLE 6

Figure 2:
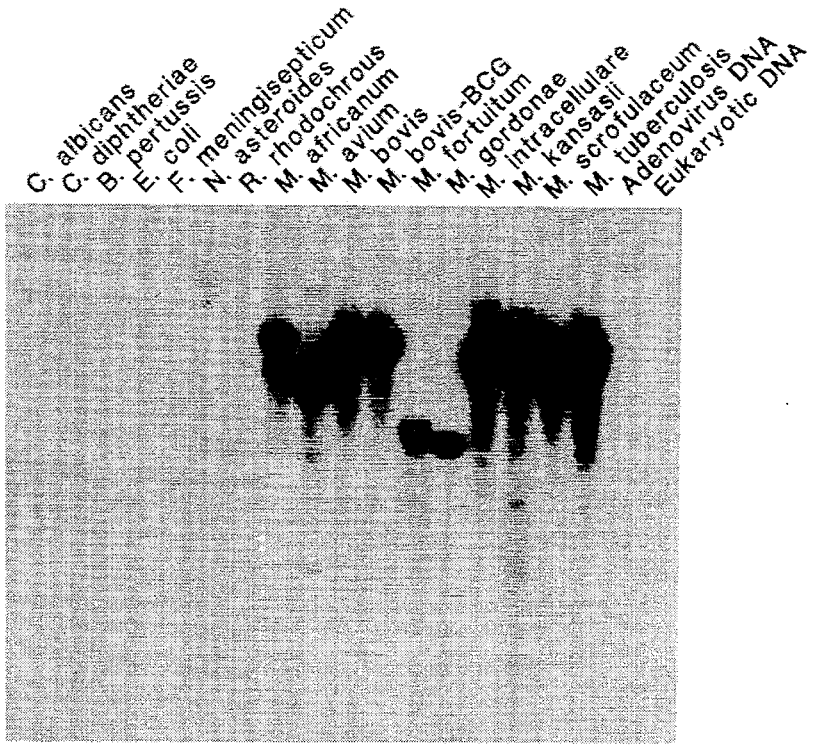
FIG. 2 shows a Southern blot of mycobacteria and non-mycobacteria which was probed with MK14-C labeled with $^{32}P$. This banding pattern shows strong genus specificity with no cross reactivity seen in any non-mycobacteria tested.
Figure 3:
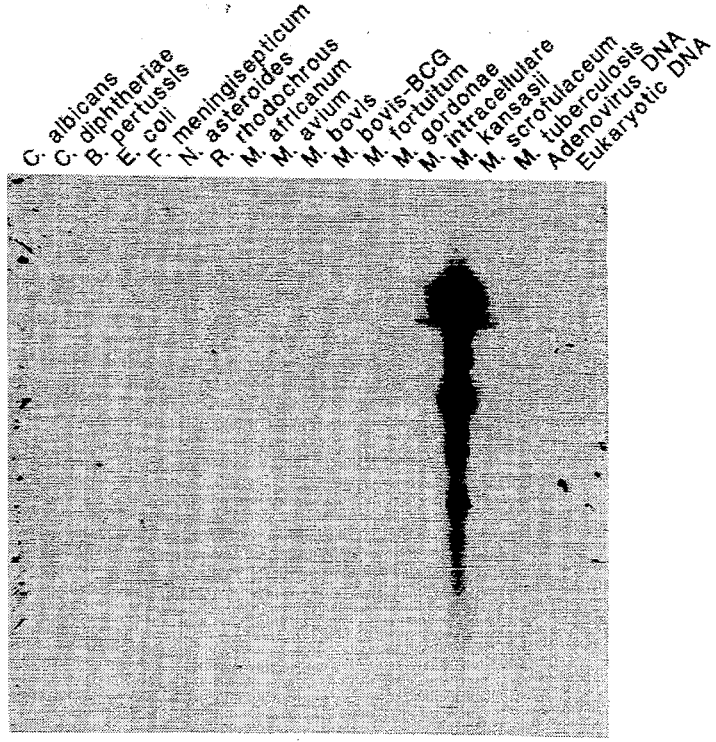
FIG. 3 shows a Southern blot of mycobacteria and non-mycobacteria which was probed with MK14-D labeled with $^{32}P$. This probe shows strong *M. kansasii* specificity and does not cross react with any other organisms tested.

Hybridization Patterns of MK14 Fragments A–E as Determined by Genomic Southern Blot Analysis MK14 fragments A–E produced in Example 5 above were used as probes for Southern blot analysis of genomic DNA from a variety of mycobacteria and non-mycobacteria. The MK14 fragments were hybridized to the genomic blots overnight at 65° C. in hybridization solution (Gibco BRL, Gaithersburg, Md.). The hybridization solution contained 6X SSC (0.9M NaCl, 0.09M Na citrate, pH 7), 0.01M EDTA, pH 8 and 5X Denhardt's solution (0.1% w/v Ficoll Type 400, 0.1% w/v polyvinylpyrrolidone, 0.1% w/v bovine serum albumin) and 100 μg/ml sheared, denatured salmon sperm DNA. SSC solutions for washing the blots were made from a 20X SSC stock solution (3M NaCl, 0.3M Na citrate, pH 7). After hybridization, the blots were rinsed in 1X SSC and washed twice in 1X SSC with 0.1% SDS for 15 min. each time at room temperature. This was followed by two washes in 1X SSC with 0.1% SDS for 15 min. each time at 65° C. and a rinse in 5X SSC. The wet blot was exposed to film overnight, then rewashed at higher stringency (twice, 15 min. each in 0.1X SSC with 0.1% SDS at 65° C.) and re-exposed overnight. All fragments produced unique hybridization patterns. Fragment C (MK14-C)(SEQ ID NO:14) showed strong genus specificity (FIG. 2), whereas fragment D (MK14-D)(SEQ ID NO:15) showed strong M. kansasii specificity (FIG. 3). Fragment A (MK14-A)(SEQ ID NO:12) hybridized to all species of Mycobacteria tested, but cross reacted to a few non-mycobacterial species. Fragment B (MK14-B)(SEQ ID NO:13) hybridized strongly to M. kansasii, hybridized weakly to TB complex organisms and M. gordonae, and showed no cross-reactivity to the non-mycobacterial species tested. Fragment E (MK14-E)(SEQ ID NO:16) hybridized well to M. bovis, M. gordonae, M. intracellulare, and M. kansasii, did not hybridize to the other mycobacterial species tested, and showed no cross-reactivity to the non-mycobacterial species tested.

For Southern blot analysis, genomic DNA was digested with PstI (GIBCO BRL). The reactions were separated on a 0.8% agarose gel then transferred to a nylon membrane (GIBCO BRL nylon-1 or NEN-DuPont Gene Screen). See J. Sambrook et al., Molecular Cloning, A Laboratory Manual (2d Ed. 1989)(Cold Spring Harbor Laboratory). Filters were then UV cross-linked (Stratalinker) and hybridized (GIBCO BRL) (Sambrook et. al.). The probes were labeled by random primers (Boehringer Mannheim Biochemicals) using [α-32P]-deoxyadenosine triphosphate and [α-32P]-deoxycytidine triphosphate (NEN-DuPont). The blots were washed at −25° C. to −10° C. below the predicted Tm. (Sambrook et. al.). The filters were exposed to XAR-5 film for 1–7 days.

EXAMPLE 7

Hybridization Patterns of MK14 Fragments C1 and C2 as Determined by Genomic Southern Blot Analysis Fragment MK14-C was divided into two smaller fragments by PCR amplification as described above with oligonucleotides MK14-13 (TAG TAT CGA CTG CGT)(SEQ ID NO:17) and MK 14-14 (TCT TGC CCG TTG GGG)(SEQ ID NO:18), and with oligonucleotides MK14-15 (CCC CAA CGG GCA AGA) (SEQ ID NO: 19) and MK14-10 (SEQ ID NO: 9) to produce fragment MK14-C1 (SEQ ID NO:20) and fragment MK14-C2 (SEQ ID NO:21) respectively. MK14-C1 hybridized to all the slow growing mycobacteria, however it failed to hybridize to, *M. fortuitum* and *M. gordonae*. Fragment MK14-C2 did hybridize to all mycobacteria tested and did not cross hybridize to the non-mycobacterial DNA's tested.

EXAMPLE 8

PCR Analysis of Fragment MK14-C

Figure 4:
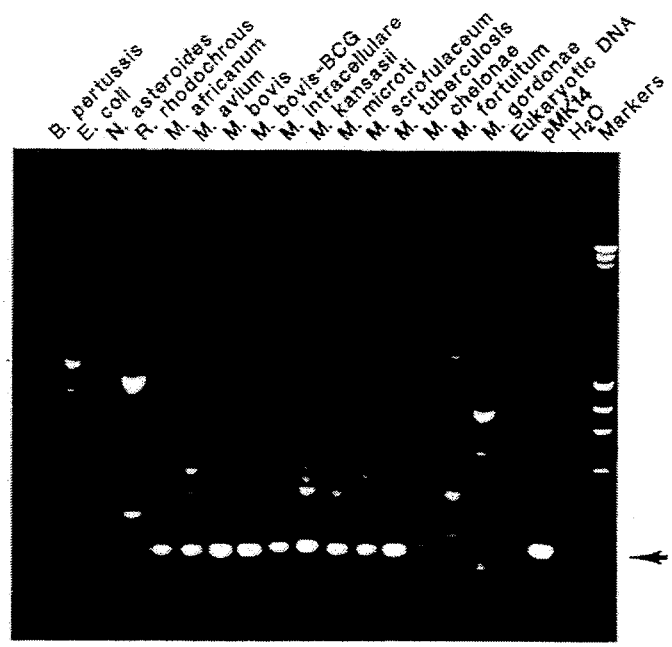
FIG. 4 shows a Polymerase Chain Reaction (PCR) agarose gel. PCR amplification reactions, using oligos 14-3 (SEQ ID NO:2) and 14-10 (SEQ ID NO:9) as primers, were analyzed by visualizing on a 1% ethidium bromide stained agarose gel. The arrow points to a 242 bp product found in all the lanes with slow growing mycobacteria used as template. As a positive control the plasmid MK14 (pMK14) was used as a template. As a negative control water was added instead of template DNA.

MK14-C was analyzed further by PCR analysis. A PCR amplification reaction containing oligos 14-3 (SEQ ID NO:2) and 14-10 (SEQ ID NO:9), using many mycobacterial and non-mycobacterial DNA's as templates, showed the best genus specificity (FIG. 4). These oligos amplify a 242 bp product containing fragments B and C (FIG. 1)(SEQ ID NO:22). There was a product of the correct size in all of the slow growing mycobacteria tested. The fast growing mycobacteria, *M. chelonae, M. fortuitum* and *M. gordonae*, did not show a 242 bp band on an ethidium bromide stained agarose gel. A specific probe to an internal region of the amplified product will show only specific products which may not be visualized on an ethidium bromide stained agarose gel. It will also prove that the 242 bp product seen in the slow growing mycobacteria is in fact the specific MK14-C-like product.

Figure 5:
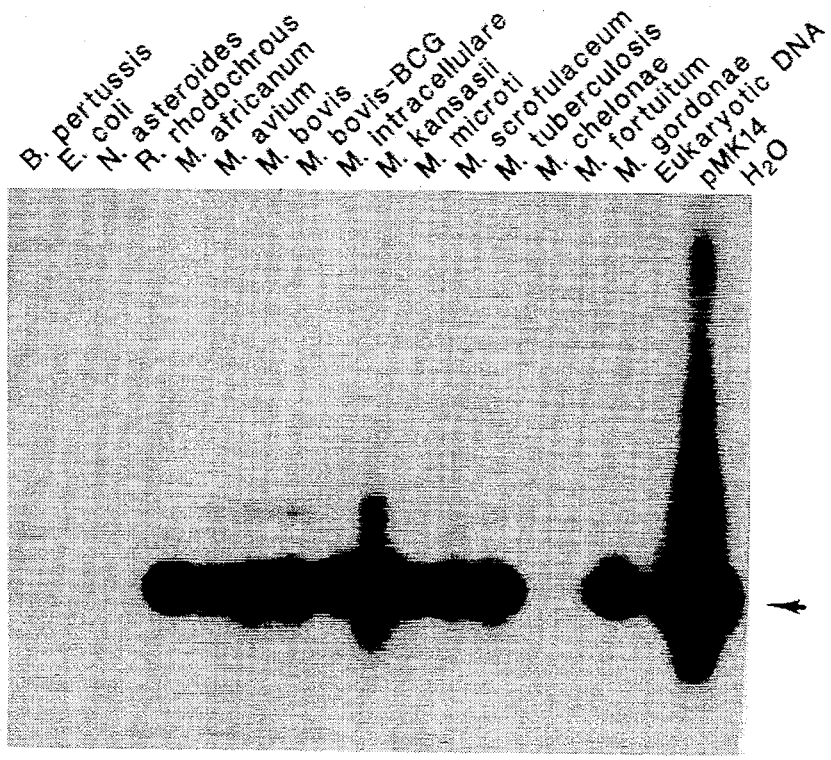
FIG. 5 shows a Southern blot of the PCR gel in FIG. 4 probed with MK14-C labeled with $^{32}P$. The arrow points to a 242 bp product present in all the slow growing mycobacteria and *M. gordonae*. It is absent in all the non-mycobacteria, and absent in mycobacteria *M. chelonae* and *M. fortuitum*. The positive and negative controls are the same as those in FIG. 4.

A southern blot was done on these PCR amplification reactions using MK14-C as the probe. PCR Southern blots were done in the same manner as the genomic southern blots described above, except 5 µl of the PCR reaction was separated on a 1.0% agarose gel. The blots were hybridized as in Example 6, rinsed in 1X SSC with 0.1% SDS and washed twice, 30 min. each time, at room temperature in 1X SSC with 0.1% SDS. This was followed by two 15 min. washes at 65° C. in 0.2X SSC with 0.1% SDS (100 ml volume) and one 15 min. wash at 65° C. with 0.2X SSC with 0.1% SDS (800 ml volume). The wet blot was then exposed to film. The probe hybridized to all the slow growing mycobacteria and *M. gordonae*. It did not hybridize to *M. chelonae, M. fortuitum, E. coli, B. pertussis, N. asteroides, R. rhodochrous* or eukaryotic DNA (FIG. 5).

EXAMPLE 9

Subcloning MK14 fragments B and C From *M. avium* and *M. Tuberculosis*

Choosing oligonucleotides that will amplify all mycobacteria is dependent on how similar the MK14-C DNA sequence is among different species. Therefore, it was decided to sequence the analogous DNA from two additional species, *M. avium* and *M. tuberculosis*. A comparison of the new sequences to the *M. kansasii* sequence could then be used to design specific oligonucleotides.

PCR amplification reactions were carried out using oligos 14-3 (SEQ ID NO:2) and 14-10 (SEQ ID NO:9) with *M. avium, M. tuberculosis* and *M. kansasii* genomic DNA as templates. The 242 bp product was isolated by Low Melting Point agarose (GIBCO BRL). They were then kinased in 50 mM Tris-HCl pH 8.8, 10 mM MgCl₂, 5% glycerol, 5mM DTT, 0.5 mM ATP and 10 Units/20 µl Polynucleotide Kinase (Stratagene) for 30 minutes at 37° C. The vector, BlueScript SK+, was digested with HincII (GIBCO BRL) then phosphatased with CIAP (Boehringer Mannheim Biochemicals). The insert and vector were ligated in a 3 to 1 ratio overnight at 15° C. Subclones of each were sequenced as described above.

Comparing *M. kansasii* fragment BC (SEQ ID NO:22) with *M. tuberculosis* fragment BC (SEQ ID NO:23) or *M. avium* fragment BC (SEQ ID NO:24), the sequence similarities are 79% and 80% respectively. Even when *M. avium* is compared to *M. tuberculosis* the sequence similarity is 76%. When all three are aligned, the homology is 69%.

EXAMPLE 10

Screening of PCR Amplification Reactions by Primer Extension with Oligos 14-23 and 14-15.

The same set of PCR amplification reactions were screened for specificity by primer extension using oligo 14-23 (FIG. 4). Oligo 14-23 (CTA GTG AAT GGG A)(SEQ ID NO:25) was designed using the sequence homology information described above. The results showed the same specificity as the Southern blots (data not shown). The varying intensities of the bands can be explained by the oligo sequence. The oligo sequence is identical in *M. tuberculosis* and *M. kansasii*, however there is one mismatch in *M. avium*.

For primer extension, 2 pmoles of oligonucleotide 14-23 was kinased in 1X REact 1 (BRL) with 4.6 pmoles of [g-$^{32}$P]-adenosine triphosphate (NEN-DuPont) and 1 unit/µl Polynucleotide Kinase (Stratagene). The reaction was incubated at 37° C. for 30 minutes then heated to 65° C. for 10 minutes. The reaction was then diluted to 2X the volume with TE (10 mM Tris/8.0, 1 mM EDTA). For the primer extension reaction 5 µl of a PCR reaction was diluted to 10 µl in 1X PCR buffer (Perkin Elmer Cetus), 125 mM dNTP's, and 0.05 pmoles/10 µl of labeled primer. The reaction was heated to 95° C. for 10 minutes then cooled to room temperature. 1.5 units of Klenow Large Fragment (BRL) was added and the samples were incubated at 37° C. for 10 minutes. Stop solution (USB) was added and the samples were heated to 95° C. for 5 minutes before separating on an 8% acrylamide denaturing gel. Gels were then exposed to XAR film for 2-16 hours.

Another primer extension reaction was done on the same PCR amplified products using oligo 14-15 (SEQ ID NO:16). This oligo has very little homology between *M. kansasii, M. tuberculosis* and *M. avium* with 6-7 mismatches in 13 bp. The only products detected were those from *M. kansasii* and the control plasmid, pMK14 (data not shown). There was also a slight band seen in *M. gordonae*. Using two different oligos to detect the same PCR amplification reaction by primer extension, gave dramatically different profiles. Oligo 14-23 showed genus specificity, whereas oligo 14-15 showed *M. kansasii* specificity. This shows the sequences provided here can be used for genus, *M. kansasii, M. tuberculosis* or *M. avium* specificity depending on the assay and detection methods used. In both the Southern blot and primer extension assays, *N. asteroides* and *M. fortuitum* showed very weak hybridization after longer exposures.

The foregoing examples are illustrative of the present invention, and are not to be construed as limiting thereof. The invention is defined by the following claims, with equivalents of the claims to be included therein.

That which is claimed is:

1. An oligonucleotide probe capable of selectively hybridizing to Mycobacteria nucleic acid, said oligonucleotide probe selected from the group consisting of:
  (a) an oligonucleotide probe consisting of a DNA sequence selected from the group consisting of DNA sequences given herein as SEQ ID NO: 1, SEQ ID NO:13, SEQ ID NO:14, SEQ ID NO:15, SEQ ID NO:16, SEQ ID NO:20, SEQ ID NO:21 and SEQ ID NO:25, and;
  (b) an oligonucleotide probe consisting of a DNA sequence selected from the group consisting of the complementary DNA sequence to any of the probes of (a) and are capable of selectively hybridizing to Mycobacteria nucleic acid.

2. An oligonucleotide probe according to claim 1 selected from the group consisting of probes consisting of the sequences given herein as SEQ ID NO:1 (MK14), SEQ ID NO:14 (MK14-C) and SEQ ID NO:21 (MK14-C2) which is capable of specifically hybridizing to nucleic acid of the genus Mycobacteria.

3. An oligonucleotide probe according to claim 1 selected from the group consisting of probes consisting of the sequences given herein as SEQ ID NO:20 (MK14-C1) and SEQ ID NO:25 which is capable of specifically hybridizing to nucleic acid of slow growing Mycobacteria.

4. An oligonucleotide probe selected from the group consisting of an oligonucleotide probe consisting of the DNA sequence given herein as SEQ ID NO:22 (*M. Kansasii* fragment BC), an oligonucleotide probe consisting of the DNA sequence given herein as SEQ ID NO:23 (*M. tuberculosis* fragment BC), and an oligonucleotide probe consisting of the sequence given herein as SEQ ID NO:24 (*M. avium* fragment BC).

5. An oligonucleotide probe according to claim 1 in which guanine plus cytosine comprise less than 70% of the total nucleotide composition of said probe.

6. A strand displacement amplification oligonucleotide probe which selectively hybridizes to Mycobacteria nucleic acid, said oligonucleotide probe consisting of:
  (a) a DNA sequence selected from the group consisting of DNA sequences given herein as SEQ ID NO:1, SEQ ID NO:13, SEQ ID NO:14, SEQ ID NO:15, SEQ ID NO:16, SEQ ID NO:20, SEQ ID NO:21, SEQ ID NO:25 and the complementary DNA sequence of SEQ ID NO:1, SEQ ID NO:13, SEQ ID NO:14, SEQ ID NO:15, SEQ ID NO:16, SEQ ID NO:20, SEQ ID NO:21, SEQ ID NO:25,
  (b) a restriction enzyme recognition site positioned 5' of the DNA sequence of (a), and
  (c) a flanking DNA sequence positioned 5' of the restriction enzyme recognition site of (b) which facilitates binding of a restriction enzyme specific for the restriction enzyme recognition site.

7. An oligonucleotide probe according to claim 1 labelled with a detectable marker.

8. An oligonucleotide probe capable of selectively hybridizing to *Mycobacteria kansasii* nucleic acid, said oligonucleotide probe selected from the group consisting of:
  (a) an oligonucleotide probe selected from the group consisting of probes consisting of the DNA sequences given herein as SEQ ID NO:15 (MK14-D) and SEQ ID NO:13, and;
  (b) an oligonucleotide probe consisting of a DNA sequence selected from the group consisting of the complementary DNA sequence to any of the foregoing oligonucleotide probes and arc capable of selectively hybridizing to *Mycobacteria kansasii* nucleic acid.

9. An oligonucleotide probe according to claim 8 consisting of the DNA sequence given herein as SEQ ID NO:15 (MK14-D).

10. An oligonucleotide probe according to claim 8 in which guanine plus cytosine comprise less than 70% of the total nucleotide composition of said probe.

11. An oligonucleotide probe according to claim 8 labelled with a detectable marker.

12. A method of detecting Mycobacteria nucleic acid in a nucleic acid sample, comprising:
  (a) contacting an oligonucleotide probe to the nucleic acid sample under conditions permitting the hybridization of said oligonucleotide probe to Mycobacteria nucleic acid, wherein said oligonucleotide probe is selected from the group consisting of
    (i) an oligonucleotide probe selected from the group consisting of probes consisting of the DNA sequences given herein as SEQ ID NO:1, SEQ ID NO:13, SEQ ID NO:14, SEQ ID NO:15, SEQ ID NO:16, SEQ ID NO:20, SEQ ID NO:21 and SEQ ID NO:25, and;
(ii) an oligonucleotide probe consisting of a DNA to any of the probes in (i) and which is capable of selectively hybridizing to Mycobacteria nucleic acid; and then
(b) detecting whether or not said oligonucleotide probe hybridizes to said nucleic acid sample, the hybridization of the oligonucleotide probe to the nucleic acid sample indicating that the nucleic acid sample contains Mycobacteria nucleic acid.

13. A method according to claim 12, wherein said nucleic acid sample is DNA.

14. A method according to claim 12, wherein said nucleic acid sample is RNA.

15. A method according to claim 12, wherein said oligonucleotide probe is labelled with a detectable marker, and wherein said detecting step is carried out by detecting said detectable marker.

16. A method according to claim 12, further comprising a strand displacement amplification step preceeding said detecting step.

17. A method according to claim 12, further comprising a polymerase chain reaction amplification step preceeding said detecting step.

18. A method according to claim 12, further comprising a ligase chain reaction amplification step preceeding said detecting step.

19. A method of selectively amplifying a target sequence present in slow growing Mycobacteria in a nucleic acid sample, comprising:
(a) contacting at least one pair of oligonucleotide probes to the nucleic acid sample under conditions permitting the hybridization of each of said oligonucleotide probes to the Mycobacteria target sequence, wherein said pair of probes together comprise an amplification pair,
said pair of oligonucleotide probes consisting of the DNA sequences given herein as SEQ ID NO:2 and SEQ ID NO:9; and
(b) amplifying said Mycobacteria target sequence by cyclically reacting said at least one pair of oligonucleotide probes with said nucleic acid sample to produce an amplification product.

20. A method according to claim 19, wherein said amplifying step is carried out by strand displacement amplification.

21. A method according to claim 19, wherein said amplifying step is carried out by polymerase chain reaction.

22. A kit for detecting Mycobacteria nucleic acid in a nucleic acid sample, comprising a hybridization solution together with an oligonucleotide probe selected from the group consisting of
(i) an oligonucleotide probe selected from the group consisting of probes consisting of the DNA sequences given herein as SEQ ID NO:1, SEQ ID NO:12, SEQ ID NO:13, SEQ ID NO:14, SEQ ID NO:15, SEQ ID NO:16, SEQ ID NO:20, SEQ ID NO:21 and SEQ ID NO:25, and;
(ii) an oligonucleotide probe consisting of a DNA sequence selected from the group consisting of the complementary DNA sequence to any of the probes of (i) and which is capable of selectively hybridizing to Mycobacteria nucleic acid.

23. A kit according to claim 22, wherein said oligonucleotide probe is lyophylized.

24. A kit according to claim 22, wherein said oligonucleotide probe is carried in said hybridization solution.

25. A kit according to claim 22, said oligonucleotide probe selected from the group consisting of probes consisting of the sequences given herein as SEQ ID NO:1, SEQ ID NO:14 and SEQ ID NO:21 and capable of selectively detecting nucleic acid of the genus Mycobacteria.

26. A kit according to claim 22, said oligonucleotide probe selected from the group consisting of oligonucleotide probes consisting of the sequences given herein as SEQ ID NO: 15 and SEQ ID NO:13 and capable of selectively detecting nucleic acid of *Mycobacterium kansasii*.

27. A kit according to claim 22, said oligonucleotide probe selected from the group consisting of an oligonucleotide probe consisting of the DNA sequence given herein as SEQ ID NO:22 (*M. Kansasii* fragment BC), an oligonucleotide probe consisting of the DNA sequence given herein as SEQ ID NO:23 (*M. tuberculosis* fragment BC), and an oligonucleotide probe consisting of the sequence given herein as SEQ ID NO:24 (*M. avium* fragment SC).

28. A kit according to claim 22, said oligonucleotide probe selected from the group consisting of probes consisting of the sequences given herein as SEQ ID NO:20 and SEQ ID NO:25 and capable of selectively hybridizing to nucleic acid of slow growing Mycobacteria.

29. A method according to claim 12 wherein the nucleic acid sample is contacted with an oligonucleotide probe selected from the group consisting of probes consisting of the sequences given herein as SEQ ID NO:1, SEQ ID NO:14 and SEQ ID NO:21 and nucleic acid of the genus Mycobacteria is detected.

30. A method according to claim 12 wherein the nucleic acid sample is contacted with an oligonucleotide probe selected from the group consisting of probes consisting of the sequences given herein as SEQ ID NO:15 and SEQ ID NO:13 and hybridization to *Mycobacteria kansasii* is detected.

31. A method according to claim 12 wherein the nucleic acid sample is contacted with an oligonucleotide probe consisting of the sequence given herein as SEQ ID NO:25 and hybridization to nucleic acid of slow growing Mycobacteria is detected.

* * * * *

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 531 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
GATCGGCTCC GGCGAACGAT TCCGCCAGGG ACGGCCGGCG CACCCCGGCC GCCGGCGTGC      60
TCACCTCAAG CCTCGGCGGC GAACCCGACG CGTCGACTCT GTGTGCCACC ACACCATCAT     120
CCGCCATGGC CGCGACCAGT TAGCCAGTTA GTGTGACGGC ACTCTTCCCG GGCTTCACCC     180
ACAGGTAGCC GATGAGCCGT ATGAGCCCCC GCACGCCGTA GTATCGACTG CGTCTAGTGA     240
ATGGGAATCG GCGGAGAGTG ACAGAGCATA TCCCGGCCCC AACGGGCAAG ACGGATGGGC     300
GCAAGCGGCG CTGGCACCAG CACAAGGTGG AGCGGCGCAA CGAACTCGTT GACGGGACAA     360
TCGAGGCCAT ACGTGTCCGC GGCCGCTTCC TGAGTATGGA CGAGATCCGT GAAGAAACC      420
CGCAGGAATG GGCGCGCATG GCTCAGGGGC AGCTGCCCAG CGCCGTCGAC GAGGATGCCT     480
TCCGCGCGCG GGTCCGCGCG GCTGTCGACC ACGTGGTCGT CAGCGCCGAT C              531
```

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
ACCTGTGTGC CACCACACCA                                                  20
```

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

```
ATACGGTCAT CGGCTACCTG                                                  20
```

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

```
AACGAACTCG TTGACGGGAC                                                  20
```

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

ATTCCTGCGG GTTTTCTTCA        20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

GGCTCCGGCG AACGATTCCG        20

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

CGACGCGTCG GGTTCGCCGC        20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

GAGCCCCCGC ACGCCGTAGT        20

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

CGCCGCTCCA CCTTGTGCTG        20

( 2 ) INFORMATION FOR SEQ ID NO:10:

( i ) SEQUENCE CHARACTERISTICS:
        ( A ) LENGTH: 20 base pairs
        ( B ) TYPE: nucleic acid ( C ) STRANDEDNESS: single
( D ) TOPOLOGY: linear ( i i ) MOLECULE TYPE: cDNA ( x i ) SEQUENCE DESCRIPTION: SEQ ID NO:10:

GGGCGCGCAT GGCTCAGGGG 20

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

GGCGCTGACG ACCACGTGGT 20

( 2 ) INFORMATION FOR SEQ ID NO:12:

( i ) SEQUENCE CHARACTERISTICS:
        ( A ) LENGTH: 91 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

GGCTCCGGCG AACGATTCCG CCAGGGACGG CCGGCGCACC CCGGCCGCCG GCGTGCTCAC 60

CTCAAGCCTC GGCGGCGAAC CCGACGCGTC G 91

( 2 ) INFORMATION FOR SEQ ID NO:13:

( i ) SEQUENCE CHARACTERISTICS:
        ( A ) LENGTH: 107 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

ACTCTGTGTG CCACCACACC ATCATCCGCC ATGGCCGCGA CCAGTTAGCC AGTTAGTGTG 60

ACGGCACTCT TCCCGGGCTT CACCCACAGG TAGCCGATGA GCCGTAT 107

( 2 ) INFORMATION FOR SEQ ID NO:14:

( i ) SEQUENCE CHARACTERISTICS:
        ( A ) LENGTH: 135 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

GAGCCCCCGC ACGCCGTAGT ATCGACTGCG TCTAGTGAAT GGGAATCGGC GGAGAGTGAC 60

AGAGCATATC CCGGCCCCAA CGGGCAAGAC GGATGGGCGC AAGCGGCGCT GGCACCAGCA 120

CAAGGTGGAG CGGCG 135

( 2 ) INFORMATION FOR SEQ ID NO:15:

( i ) SEQUENCE CHARACTERISTICS:
        ( A ) LENGTH: 92 base pairs ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

CAACGAACTC GTTGACGGGA CAATCGAGGC CATACGTGTC CGCGGCCGCT TCCTGAGTAT     60

GGACGAGATC CGTGAAGAAA ACCCGCAGGA AT     92

( 2 ) INFORMATION FOR SEQ ID NO:16:

( i ) SEQUENCE CHARACTERISTICS:
            ( A ) LENGTH: 98 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:16:

GGGCGCGCAT GGCTCAGGGG CAGCTGCCCA GCGCCGTCGA CGAGGATGCC TTCCGCGCGC     60

GGGTCCGCGC GGCTGTCGAC CACGTGGTCG TCAGCGCC     98

( 2 ) INFORMATION FOR SEQ ID NO:17:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:17:

TAGTATCGAC TGCGT     15

( 2 ) INFORMATION FOR SEQ ID NO:18:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:18:

TCTTGCCCGT TGGGG     15

( 2 ) INFORMATION FOR SEQ ID NO:19:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:19:

CCCCAACGGG CAAGA     15

( 2 ) INFORMATION FOR SEQ ID NO:20:

( i ) SEQUENCE CHARACTERISTICS:
            ( A ) LENGTH: 73 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:20:

| TAGTATCGAC | TGCGTCTAGT | GAATGGGAAT | CGGCGGAGAG | TGACAGAGCA | TATCCCGGCC | 60 |
| CCAACGGGCA | AGA | | | | | 73 |

( 2 ) INFORMATION FOR SEQ ID NO:21:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

| CCCCAACGGG | CAAGACGGAT | GGGCGCAAGC | GGCGCTGGCA | CCAGCACAAG | GTGGAGCGGC | 60 |
| G | | | | | | 61 |

( 2 ) INFORMATION FOR SEQ ID NO:22:

( i ) SEQUENCE CHARACTERISTICS:
        ( A ) LENGTH: 241 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:22:

| ACCTGTGTGC | CACCACACCA | TCATCCGCCA | TGGCCGCGAC | CAGTTAGCCA | GTTAGTGTGA | 60 |
| CGGCACTCTT | CCCGGGCTTC | ACCCACAGGT | AGCCGATGAG | CCGTATGAGC | CCCCGCACGC | 120 |
| CGTAGTATCG | ACTGCGTCTA | GTGAATGGGA | ATCGGCGGAG | AGTGACAGAG | CATATCCCGG | 180 |
| CCCCAACGGG | CAAGACGGAT | GGGCGCAAGC | GGCGCTGGCA | CCAGCACAAG | GTGGAGCGGC | 240 |
| G | | | | | | 241 |

( 2 ) INFORMATION FOR SEQ ID NO:23:

( i ) SEQUENCE CHARACTERISTICS:
        ( A ) LENGTH: 230 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

| ACCTGTGTGC | CACCACACCA | TCATCCGCTA | TCACCGGCAC | CAGTTAATGT | GACGACACTG | 60 |
| TCCTGCGCAC | CCCGCCGSCG | CGTCCAATGT | GCCAGCAGGA | CCCCAATTG | GCCGTAGTAT | 120 |
| CGGGAGCGTC | TAGTGAATGG | GAATTGGCAA | CAGTGGCAGA | GCGTATCCCG | GCCGTGACCG | 180 |
| TGAAGACGGA | TGTGCAAGCG | ACGCTGGCAC | CAGCACAAGG | TGGAGCGGCG | | 230 |

( 2 ) INFORMATION FOR SEQ ID NO:24:

( i ) SEQUENCE CHARACTERISTICS:
        ( A ) LENGTH: 230 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

```
ACCTGTGTGC  CACCACACCA  TCATCTATST  TTCCCGCCGA  TTGGTGTGAC  GACACCGCGC        60

GCGACGGTCG  TCCACGCCCG  GGCCAAGACC  GCGAACCAGC  CGGTCCACGC  CGTAGTATCG       120

AGGGCGTCTA  GGGAATGGGA  TTTGGCGATA  GTGGCAGAGC  AAATCACGGC  TGCGAGCGTC       180

AAAATGGACG  GGCGCAAGCG  GCGCTGGCAT  CAGCACAAGG  TGGAGCGGCG                   230
```

( 2 ) INFORMATION FOR SEQ ID NO:25:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

```
CTAGTGAATG  GGA                                                              13
```